United States Patent [19]
Rautenstrauch et al.

[11] Patent Number: 5,874,600
[45] Date of Patent: Feb. 23, 1999

[54] RUTHENIUM CATALYSTS AND THEIR USE IN THE ASYMMETRIC HYDROGENATION OF CYCLOPENTENONES

[75] Inventors: Valentin Rautenstrauch, Bernex, Switzerland; Koenraad P. M. Vanhessche, Union City, N.J.; Jean-Pierre Genet, Verrieres Le Buisson; Jean-Yves Lenoir, Rouen, both of France

[73] Assignee: Firmenich SA, Geneva, Switzerland

[21] Appl. No.: 875,335

[22] PCT Filed: Nov. 20, 1996

[86] PCT No.: PCT/IB96/01263

§ 371 Date: Jul. 10, 1997

§ 102(e) Date: Jul. 10, 1997

[87] PCT Pub. No.: WO97/18894

PCT Pub. Date: May 29, 1997

[30] Foreign Application Priority Data

Nov. 22, 1995 [CH] Switzerland ............... 3300/95
Jun. 28, 1996 [CH] Switzerland ............... 1621/96

[51] Int. Cl.$^6$ ............... C07F 15/00; C07C 69/74
[52] U.S. Cl. ............... 536/136; 556/21; 560/121; 560/122
[58] Field of Search ............... 556/21, 136; 560/121, 560/122

[56] References Cited

FOREIGN PATENT DOCUMENTS

| 0 470 756 | 2/1992 | European Pat. Off. . |
| 2 693 190 | 1/1994 | France . |
| 6 918228 | 6/1971 | Netherlands . |
| 91 02588 | 3/1991 | WIPO . |
| 96 00206 | 1/1996 | WIPO . |

*Primary Examiner*—Gary Geist
*Assistant Examiner*—Brain J. Davis
*Attorney, Agent, or Firm*—Pennie & Edmonds LLP

[57] ABSTRACT

A catalyst of ruthenium (II) which includes bidentate phosphine ligands. The catalyst is obtainable by a process which includes the steps of treating equimolar amounts of an appropriate Ru(II) complex and a bidentate diphosphine ligand with an acid of formula HX, wherein X is a non-coordinating anion. The acid is used in a ratio which does not exceed 2 molar equivalents per mole of Ru(II) complex and the treatment is carried out in a non-coordinating or weakly coordinating solvent and under an inert atmosphere. This catalyst is useful for the preparation of the preferred isomer of HEDIONE, having the (+)-(1R)-cis-configuration.

26 Claims, No Drawings

RUTHENIUM CATALYSTS AND THEIR USE IN THE ASYMMETRIC HYDROGENATION OF CYCLOPENTENONES

TECHNICAL FIELD

The present invention relates to the field of asymmetric hydrogenation in homogeneous conditions and, more particularly, to the use of novel Ru(II) chiral catalysts for the asymmetric hydrogenation of cyclopentenone derivatives having the general formula

wherein $R^1$ represents a linear or branched $C_1$ to $C_4$ alkyl radical and $R^2$ represents a saturated or unsaturated, linear or branched, $C_1$ to $C_8$ hydrocarbon radical.

The compounds of formula (II) are substrates the asymmetric and stereospecific hydrogenation of which had proved heretofore impossible as a result of their weak donor capability and of their hindered structure, and this in spite of all the progress in homogeneous catalysis achieved in recent years.

PRIOR ART

A great number of chiral catalysts useful for asymmetric hydrogenations is in fact known at present. In the context of the present invention, we can cite in particular the efforts of two research groups which actively studied the synthesis of Ru(II) chiral catalysts, obtained from the Ru(II) complex of formula [(COD)Ru(2-methylallyl)$_2$](COD=cyclo-1,5-octadiene).

Thus, J.-P. Genet and his collaborators have published work related to catalysts of formula [Ru(P*—P*)(2-methylallyl)$_2$], wherein P*—P* represents a bidentate ligand of the type of those currently known under abbreviated designations such as DIOP, CHIRAPHOS, PROPHOS, BDPP, CBD, NORPHOS, DEGUPHOS, BPPM, BINAP, R-DuPHOS (R=methyl or ethyl), BIPHEMP or yet DIPAMP (see, for example, J.-P. Genet et al., Tetrahedron: Asymmetry 1991, 2, 43). Such catalysts were obtained by heating the above-mentioned Ru(II) complex together with the appropriate diphosphine ligand, in a solvent such as hexane or toluene, such as to replace the cyclooctadiene with the chiral phosphine.

Upon subsequent work (see, for example, WO 91/02588; J.-P. Genet, Acros Organics Acta, 1994, 1, 1–8; J.-P. Genet et al., Tetrahedron : Asymmetry, 1994, 5, 665– 690), these authors described the transformation of such catalysts via protonation by means of aqueous acids such as HBr, HCl, HF or $HBF_4$, in strongly coordinating solvents, capable of playing a role in stabilizing the coordination structure around the metal, which structure, according to the same authors, is of the hexacoordinate type. This kind of catalysts, which can be prepared in situ, proved to be useful for the asymmetric hydrogenation, in protic or strongly electron-donating solvents (methanol, ethanol, THF, or their mixtures with other solvents), of substrates comprising carbonyl groups and acyclic ethylenic bonds.

Other studies (see, for example, F. Heiser et al., Tetrahedron: Asymmetry, 1991, 2, 51–62; EP 643 052; EP 398 132; EP 570 674) have resulted in reports of the use of catalysts prepared in situ for hydrogenating a variety of substrates, starting from the same ruthenium complex, but following a process according to which a mixture of said complex and an appropriate diphosphine ligand is treated with namely $CF_3COOH$, once again in an electron-donor solvent able to stabilize the coordinating structure of the metal.

These catalysts, and others obtained according to similar processes described in the cited references, reveal themselves very efficient in the asymmetric hydrogenation of various substrates, often good electron-donor substrates capable of coordinating the Ru(II), and are typically used with protic solvents, or mixtures of protic and aprotic solvents. However, they proved to be inefficient with regard to the hydrogenation of substrates (II) cited above, when prepared according to the prior art methods and used under the reported conditions. In fact, substrates (II) are weak electron-donors, when compared to the type of substrates described in the prior art, and the many attempts carried out heretofore in an effort to asymmetrically hydrogenate them had always proved fruitless.

It should be pointed out that, among the formula (II) substrates, methyl 3-oxo-2-pentyl-1-cyclopentene-1-acetate is particularly interesting in the context of the invention, inasmuch as its asymmetric hydrogenation could potentially provide, in a single step, the optically active isomers of methyl dihydrojasmonate or Hedione® (origin: Firmenich SA, Geneva, Switzerland), a prized perfuming ingredient.

Amongst the four possible Hedione® stereoisomers, methyl (+)-(1R)-cis-3-oxo-2-pentyl-1-cyclopentaneacetate is known to possess at their best the odor characters, and namely the jasmine note, for which Hedione® is prized, the strength of this isomer's odor being also superior to that of the other isomers by several orders of magnitude. Therefore, the production of methyl (+)-(1R)-cis-3-oxo-2-pentyl-1-cyclopentaneacetate in an optically pure state, or of isomer mixtures which contain essentially this isomer, is of capital importance in the fragrance industry. Yet, there is at present no synthesis of this compound which is susceptible of industrial application, starting from a substrate such as cited above, all efforts to asymmetrically hydrogenate said substrate having met with failure up until now.

DESCRIPTION OF THE INVENTION

The aim of the present invention is to provide precisely a solution to this problem.

We have now discovered that this preferred isomer of Hedione® can be prepared in excellent diastereochemical and enantiomeric purity, by way of a one-step process, resorting to the use of novel Ru(II) chiral catalysts, produced by means of an original method.

An object of the present invention is therefore a ruthenium (II) catalyst comprising bidentate phosphine ligands, characterized in that said catalyst is obtainable by a process which comprises treating equimolar amounts of an appropriate Ru(II) complex and a bidentate diphosphine ligand with an acid of the formula HX, wherein X is a non-coordinating anion, said acid being used in a ratio which does not exceed 2 molar equivalents per mole of Ru(II) complex and the treatment being carried out in a non-coordinating or weakly coordinating solvent and under an inert atmosphere.

By an "appropriate Ru(II) complex" it is meant here any Ru(II) complex wherein the metal is surrounded by dienyl and alkyl type ligands, such that the metal is σ-bonded to two of said ligands, which ligands further possess at least one bond π-bonded to the metal, two other metal coordination positions being π-bonded to the same said two ligands or to a distinct ligand.

Several ruthenium compounds, or analogous compounds of other transition metals, are known from the prior art which comprise ligands fulfilling the above-mentioned conditions and which are convenient as precursors of the catalysts of the present invention.

One can cite more particularly, as appropriate ruthenium (II) complexes, the compounds of the [(diene)Ru(allyl)$_2$] type, wherein "diene" stands for example for COD (cycloocta-1,5-diene) or NBD (norbornadiene), or yet hepta-1,4-diene, and "allyl" represents a 2-propenyl or 2-methallyl radical (see, for instance, J.-P. Genet et al., cited references; M. O. Albers et al., Inorganic Synth. 1989, 26, 249; R. R. Schrock et al., J. Chem. Soc. Dalton Trans, 1974, 951). Other appropriate ruthenium(II) complexes include the compounds of the [bis(pentadienyl)Ru] type, wherein "pentadienyl" represents a 2,4-dimethylpentadienyl, 2,3,4-trimethylpentadienyl, 2,4-di(tert-butyl) pentadienyl or yet 2,4-dimethyl-1-oxapentadienyl radical (see, for example, R. D. Ernst et al., J. Organometallic Chem., 1991, 402, 17; L. Stahl et al., Organometallic 1983, 2, 1229 ; T. Schmidt et al., J. Chem. Soc. Chem. Commun., 1991, 1427; T. D. Newbound et al., Organometallics, 1990, 9, 2962).

Following a preferred embodiment of the catalysts of the invention, there is used as the Ru(II) precursor, the compound of formula [(COD)Ru(2-methallyl)$_2$], the bis(2,4-dimethylpentadienyl)ruthenium (e.g. L. Stahl et al. or T. D. Newbound et al., refs cited) or the bis(2,4-dimethyl-1-oxapenta-dienyl)ruthenium complexes (e.g. T. Schmidt et al., ref. cited).

Among the bidentate phosphines which can be used as ligands in the catalysts of the invention, there can be cited, as preferred embodiments, those selected from the group consisting of the chiral phosphines known under the abbreviations of Me-DuPHOS, Et-DuPHOS, BINAP, To1BINAP, SKEWPHOS, DIPAMP and CHIRAPHOS, the structures of which are represented hereafter for one of the enantiomers in particular:

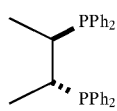

(R,R)-(+)-CHIRAPHOS
(L1)

Ph = phenyl

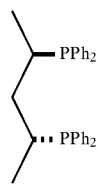

(R,R)-(+)-SKEWPHOS
(L2)

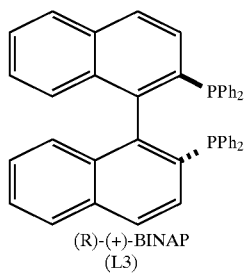

(R)-(+)-BINAP
(L3)

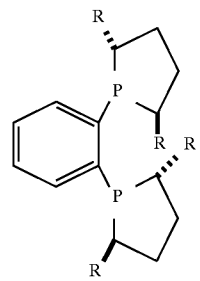

R = Me: (R,R)-(−)-Me-DuPHOS
R = Et: (R,R)-(−)-Et-DuPHOS
R = Propyl: (R,R)-(−)-Pr-DuPHOS
R = iso-Propyl: (S,S)-(−)-iPr-DuPHOS
(L4)

Ph = phenyl

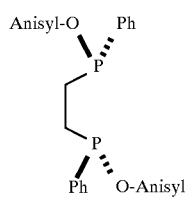

(S,S)-(+)-DIPAMP
(L5)

Other chiral bidentate phosphines which can be used in the chiral catalysts of the invention include for instance those known under the name of NORPHOS, or yet analogues of the DuPHOS type ligands, so-called "BPE", the structures of which are represented hereafter for one of the enantiomers.

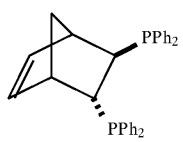

(R,R)-(−)-NORPHOS
(L6)

Ph = phenyl

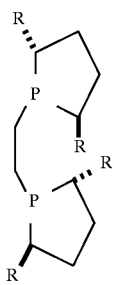

BPE
(L7)

R = alkyl radical from $C_1$ to $C_4$,
linear or branched

Other particularly useful ligands for the preparation of the catalysts of the invention are the chiral diphosphines of formula:

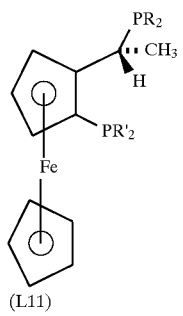

R = tert-butyl, R' = phenyl
or R = R' = cyclohexyl
or R = R' = cyclohexyl, phenyl
or R ≠ m-tolyl, R' = phenyl (L11)

in particular that known under the designation of (R)-(S)-JOSIPHOS (R=cyclohexyl, R'=phenyl) or (−)-JOSIPHOS.

Moreover, it has been ascertained that other ligands, chiral or achiral, can be used to prepare the catalysts according to the invention, which catalysts proved capable of catalyzing the hydrogenation of substrates (II) with a cis stereoselectivity above 80% and, in most cases, 95%. To this end, there can be cited the achiral or racemic bidentate ferrocenyl-diphosphines such as represent hereafter:

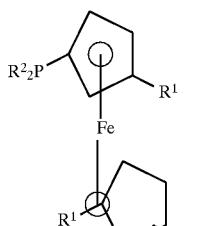

(L8)

$R^1$ = linear or branched alkyl radical from $C_1$ to $C_4$, to trimethylsilyl radical
$R^2$ = linear or branched alkyl radical from $C_1$ to $C_4$, or aryl or alkylaryl radical

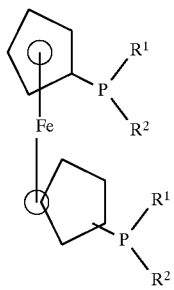

(L9)

$R^1 \neq R^2$
$R^1$ = linear or branched alkyl radical from $C_1$ to $C_4$, aryl or alkylaryl radical
$R^2$ = linear or branched alkyl radical from $C_1$ to $C_4$, aryl or alkylaryl radical Other bidentate phosphines useful as ligands are represented below:

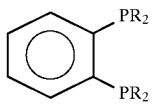

(L12)

R has the meaning indicated for (L10) above

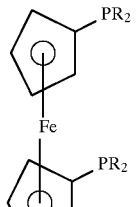

(L10)

R represents an alkyl radical from $C_1$ to $C_4$, linear or branched, an aryl radical or an alkylaryl radical

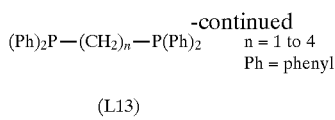

(L13)

More generally, one can use as ligands in the catalysts of the invention any bidentate diphosphine comprising substituent groups capable of rendering said diphosphine sufficiently electron-rich to allow it to stabilize the metal, without however depriving said metal from its ability to coordinate substrate (II).

It has also been observed that the diphosphines having a certain number of alkyl or cycloalkyl type substituents revealed themselves particularly useful for the aim of the invention and provided catalysts which were very active and efficient for the hydrogenation of substrates (II).

It is apparent from the above that the preferred ligands for preparing the catalysts of the invention are diphosphine ligands in which the two phosphorous atoms are bridged by groups of the alkyl, 1,2-benzenyl, bis(naphtalenyl) or yet 1,1'-ferrocenyl type, optionally substituted, said phosphorous atoms further carrying two other substituents, which can be identical or different and formed of alkyl, aryl or alkylaryl radicals, or yet alicyclic radicals.

The catalysts of the invention which comprise diphosphine ligands of the DuPHOS, BINAP, Tol BINAP, SKEWPHOS or JOSIPHOS type are particularly advantageous as catalysts for the asymmetric hydrogenation of the substrates of formula (II), as is apparent from the examples presented further on.

Amongst the latter catalysts, those which comprise ligands of the SKEWPHOS, JOSIPHOS or Me-DuPHOS type showed themselves capable of particularly advantageous performances and are therefore preferred according to the invention. (R,R)-(−)-Me-DuPHOS, or (−)-1,2-bis(2,5-dimethylphospholano)benzenyl made it possible to obtain choice catalysts according to the invention.

The ligands of the type L1 to L13 represented below are either commercially available compounds or they can be prepared according to processes analogous to previously described methods.

For example, the ligands of the DuPHOS, SKEWPHOS, BINAP, CHIRAPHOS, DIPAMP and NORPHOS type are mostly commercial products and, in any event, they can be obtained via processes described in the literature, namely in reference works such as the books of R. Noyori, Asymmetric Catalysis in Organic Synthesis, John Wiley & Sons, N.Y (1994), Chap. II and J. Ojima, Catalytic Asymmetric Synthesis, VCH Publishers, N.Y. (1994), Chap. I.

The L13 ligands are very common and commercialized, whereas those which contain ferrocenyl groups are either commercialized (such is the case for example of the compound of structure L10 wherein R represents a phenyl radical), or they can be prepared by methods analogous to those described for example by M. D. Rausch et al., J. Organometallic Chem. 1967, 10, 127, R. A. Brown et al. 1992, 20, 2611 and G. Herberich et al., Chem. Ber. 1995, 128, 689. Moreover, some of these ferrocenyldiphosphine type ligands are novel compounds which are also the object of the invention. Such is the case namely of the ligands of formula (L8) wherein $R^1$=trimethylsilyl and $R^2$=isopropyl.

The ligands of the (L11) type wherein R=cyclohexyl et R'=phenyl, known under the designation of JOSIPHOS, can be prepared as is described by A. Togni et al., J. Amer. Chem. Soc. 1994, 116, 4062. They are also commercially available, and the same applies to their analogues (origin: STREM Chemicals, Inc.).

The above-mentioned acids of formula HX, used for the preparation of the catalysts of the invention, are typically used in the form of the corresponding etherates (for example $HBF_4.R_2O$, $R=CH_3$ or $C_2H_5$) or of any other onium type salt (phosphonium or sulfonium, for example). These etherates are commercial products, or they can be prepared from the corresponding silver salts, by reacting with HCl. In the latter case, the silver salt, for example $AgBF_4$, $AgPF_6$, $AgSbF_6$ or $AgAsF_6$ will be typically reacted with HCl, in a solvent containing a dialkylether, for example a mixture of dichloromethane and diethylether. As the silver chloride precipitates, it provides the etherate solution of the acid, with is then used according to the invention in the reaction with the ruthenium complex and the phosphine ligand.

Thus, as the HX acid, one can cite an acid selected from the group consisting of $HBF_4$, $HPF_6$, $HSbF_6$, $HAsF_6$, and $HB[3,5-(CF_3)_2C_6H_4]_4$. All these acids have as common characteristic the fact that their anion is non-coordinating.

According to a preferred embodiment of the catalyst of the invention, there is used tetrafluoroboric acid etherate.

The reaction which characterizes the process for the preparation of the invention's catalysts takes place in a non-coordinating or weakly coordinating medium, under inert atmosphere. By the latter, one means here an atmosphere whose oxygen content is lower than 200 ppm and, preferably, not above 5 to 10 ppm.

By non-coordinating or weakly coordinating medium, it is meant here for example, a non-coordinating or weakly coordinating solvent. It may also be meant moreover that the reaction occurs in a solvent as defined above, but also in the presence of the above-cited substrate of formula

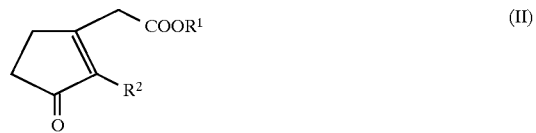 (II)

wherein $R^1$ represents a linear or branched $C_1$ to $C_4$ alkyl radical and $R^2$ represents a saturated or unsaturated, linear or branched, $C_1$ to $C_8$ hydrocarbon radical.

It has yet been ascertained that useful catalysts could also be obtained in the absence of the solvent, i.e. in the presence of the substrate of formula (II) alone. We observed that, surprisingly, the presence of said substrate also allowed the formation of Ru(II) dicationic species which were themselves capable of catalyzing the hydrogenation of the above-mentioned products (II) under the conditions which are the object of the present invention and which will be described in detail hereafter.

When the treatment of the Ru(II) complex and the diphosphine ligand, which may be a chiral one, with the HX-acid is carried out in a solvent, the latter will be preferably selected from the group consisting of dichloromethane, dichloroethane, ethyl pivalate, methyl acetate, ethyl acetate, isopropyl acetate, acetone, 2-butanone, 3-pentanone and any mixture of two or several of these solvents.

According to a preferred embodiment, dichloromethane or a mixture of the latter with other, non-coordinating or weakly coordinating solvents, in particular those mentioned above, is used.

It should be pointed out that the use of the coordinating solvents which are typically employed in the preparation of the prior art catalysts did not make it possible to obtain catalysts which, in the course of their application in the hydrogenation of the appropriate substrate (II), are capable of providing essentially the above-mentioned preferred isomer of Hedione®, as is clearly evident from the examples given below. This, unlike what we could observe with the catalysts of the present invention.

Now, the structure of the dicationic complexes of Ru(II) according to the present invention is not known. Without wanting to prejudge their exact structural nature, it seems nevertheless quite probable that they obey a formula of the type [(diene)Ru(P*—P*)S$_2$]$^{2+}$(anion$^-$)$_2$, wherein the ligand S represents the solvent (for example CH$_2$Cl$_2$ and/or ether), the substrate or a mixture of both, and P*—P* represents a bidentate phosphine ligand, which may be chiral. In fact, given the weak electron-donor character of the solvent and/or of substrate (II), and considering what is known from the prior art, it is totally surprising to observe the formation and any hydrogenation activity of these catalysts, when the coordination structure around the metal cannot be entirely defined on the basis of the general knowledge in the art, by analogy to the catalysts which have been prepared according to the known methods.

These new catalysts proved of excellent efficiency there where the catalysts which had been prepared according to the methods described in the prior art failed. We found, in fact, that their use for the hydrogenation, as the case may be asymmetric, of the compounds of formula (II) made it possible to obtain isomers of the compounds of formula

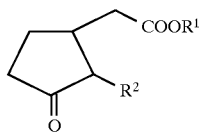

(I)

in which R$^1$ and R$^2$ have the meaning indicated above, essentially in a cis configuration and, optionally, in an enantioselective manner, as a function of the chirality of the catalyst, and with excellent optical purity.

More particularly, we were able to obtain methyl (+)-(1R)-cis-3-oxo-2-pentyl-1-cyclopentaneacetate with a cis purity above 98% and an enantiomeric excess of at least 60%.

Among these catalysts, and as is apparent from the examples presented further on, those which were obtained starting from the complex of formula [(COD)Ru(2-methallyl)$_2$] and the (-)-Me-DuPHOS or (-)-JOSIPHOS ligand, using HBF$_4$-etherate in a medium of dichloromethane, or its mixtures with methyl 3-oxo-2-pentyl-1-cyclopentene-1-acetate, proved to be particularly advantageous for the preparation of (+)-cis-Hedione®.

The catalysts comprising the chiral ligands previously cited proved to be particularly useful for the preparation of optically active compounds of formula (I), in particular of methyl (+)-(1R)-cis-3-oxo-2-pentyl-1-cyclopentaneacetate.

Of course, the use of the enantiomers of the above-cited ligands enables the preparation of the (-)-(1S)-configuration enantiomer of methyl cis-3-oxo-2-pentyl-1-cyclopentaneacetate, as the optical configuration of the catalyst determines that of the hydrogenation product of substrate (II).

According to the invention, the preparation of the catalyst can take place at room temperature or a lower temperature. Moreover, the temperature of the above-mentioned treatment does not seem to be a critical parameter of the process, susceptible of affecting the catalyst's properties and its efficiency in the hydrogenation of the substrates (II). The application of room temperature is of course advantageous from a practical point of view.

On the other hand, we observed that the ratio between the molecular weight of the HX acid, for example HBF$_4$, HPF$_6$, HSbF$_6$ ou HAsF$_6$, and the molecular weight of the ruthenium complex is a critical parameter which determines the catalyst's characteristics and its efficiency in the asymmetrical hydrogenation of the above-mentioned substrates according to the present invention, and more particularly of methyl 3-oxo-2-pentyl-1-cyclopentene-1-acetate. This is all the more surprising in that the prior art is totally silent on this subject. Actually, known studies often report the use of a substantial excess of acid, relative to the amount required to form the cationic ruthenium complex in the presence of the bidentate phosphine ligand.

Now, we have ascertained that the use of an excess of acid renders the catalysts inactive or inefficient in the context of the present invention. As is apparent from the examples below, it may even prove to be advantageous to use the acid in a ratio which is inferior to the stoechiometric amount. Thus the acid will be preferably used in a ratio from 1.5 to 2 mole equivalents, per mole of the Ru(II) complex. More preferably, the ratio between these two reagents will be about 2 mole equivalents of acid per mole of complex.

Likewise, the equimolar ratio between the appropriate Ru(II) complex and the bidentate diphosphine also seems a critical parameter of the invention.

The invention also concerns a process for the preparation of Ru(II) catalysts, characterized in that equimolar amounts of an appropriate Ru(II) complex and a bidentate diphosphine ligand are reacted, under an inert atmosphere and in a non-coordinating or weakly coordinating medium, with an acid of formula HX, wherein X is a non-coordinating anion, the acid being employed in a ratio which does not exceed 2 molar equivalents per mole of Ru(II) complex.

As previously mentioned, the appropriate Ru(II) complexes, and in particular the preferred complex [(COD)Ru(2-methylallyl)$_2$], which are used as starting products in the process for the preparation of the catalysts according to the present invention, are typically known compounds which can be prepared as is described in the above-cited prior art documents, or by processes which are analogous to those known.

On the other hand, the phosphines which form the ligands of the catalyts according to the present invention, and which determine their chirality, are either commercially available compounds or can be prepared by known methods.

As cited above, the preparation of the catalyst can be executed in a medium which is constituted by a solvent or a mixture of the solvent with the substrate (II). This last embodiment, as well as that according to which the catalyst is prepared in the presence of only the substrate (II), are methods particularly suitable for the in situ preparation of the catalysts, in the medium of the hydrogenation reaction, described further on.

The catalysts according to the present invention thus prepared are obtained as solutions in the solvent and/or the substrate (II) of the product which is the result of the reaction of the Ru(II) complex with the diphosphine ligand and the HX acid. These catalytic solutions may be used as such for the asymmetric hydrogenation of substrates (II). They can be kept under an inert atmosphere and will stay active for several days. Moreover, they may also be concentrated under vacuo to give the catalysts in a solid form.

The catalysts can also be generated in situ in the hydrogenation medium, as will become apparent below.

In this process, the order in which the reagents are mixed does not seem to have a critical impact on the properties of the resulting catalysts. Thus, we found that it was possible to first mix the Ru(II) precursor, for example [(COD)Ru(2-methallyl)$_2$], with the diphosphine ligand, in particular (-)-Me-DuPHOS, in a solvent, typically dichloromethane, and add thereafter to this mixture the selected acid, for example HBF$_4$ (in the form of its etherate), optionally dissolved in dichloromethane. Catalytic solutions according to the present invention are thus obtained, having a variable concentration in the catalyst according to the present invention, for example of the order of 0.01M (0.01 moles of catalyst/l of catalytic solution), which proved to be very advantageous in the hydrogenation of substrates (II).

Alternatively, very good catalysts were also obtained by first mixing the diphosphine ligand, in particular (−)-Me-DuPHOS, with the acid of formula HX, in the form of an etherate or an onium salt, in particular $HBF_4$-etherate, for example in dichloromethane. The product thus obtained may be reduced to the form of a solid onium salt by removing under vacuo the ether and $CH_2Cl_2$, and thereafter be used in the reaction with the Ru(II) complex in a solvent to give the desired catalysts. This embodiment is quite useful in practice, as it allows separate preparation of the salts of the ligands, which thereafter can react with the Ru(II) complex.

The dicationic compounds of Ru(II) according to the invention prove to be very useful as catalysts in hydrogenation reactions. In particular, they show an excellent efficiency in the conversion of substrates (II), and the invention therefore also concerns a process for the preparation of a compound of formula

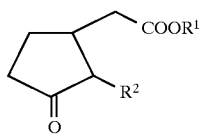 (I)

in which $R^1$ represents a linear or branched alkyl radical from $C_1$ to $C_4$ and $R^2$ represents a saturated or unsaturated hydrocarbon rest, linear or branched, from $C_1$ to $C_8$, essentially in the form of an isomer of cis configuration, characterized in that a substrate of formula

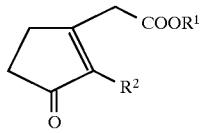 (II)

in which $R^1$ and $R^2$ have the meaning indicated above, is catalytically hydrogenated in the presence of a Ru(II) catalyst according to the present invention as previously described, and at a hydrogen pressure of from 10 to 100 bar (2 to $10 \times 10^6$ Pa).

According to a preferred embodiment of the invention, the catalyst is generated in situ before the hydrogenation of substrate (II) or, optionally, in the presence of the latter, by treating equimolar amounts of the Ru(II) complex, in particular the compound of formula [(COD)Ru(2-methylallyl)$_2$], and an appropriate chiral bidentate phosphine ligand, selected, for example, from the group consisting of the diphosphines which are known under the abbreviations of Me-DuPHOS, Et-DuPHOS, BINAP, Tol BINAP, SKEWPHOS, DIPAMP, CHIRAPHOS and JOSIPHOS, with the etherate of tetrafluoroboric acid in a proportion of about 2 molar equivalents of $HBF_4$ per mole of Ru(II) complex. This preferred embodiment enables the preparation of the above-mentioned compound (I) in the form of an optically active isomer of (1R)-cis configuration.

All the racemic or achiral ligands mentioned above provide catalysts which make it possible to obtain the compounds (I) in the form of the racemic cis-isomer. Of course, in the case of racemic ligands (for example L8 and L9), their corresponding enantiomers can be obtained by separation of the racemic ligand, and these enantiomers of the ligand may thereafter serve to prepare optically active catalysts according to the invention.

When the preparation of the catalyst takes place in the absence of substrate (II), it is preferred to first prepare the mixture of the Ru(II) complex and the diphosphine ligand, as a solution in a non-coordinating or weakly coordinating solvent, and to add to this solution the acid comprising the non-coordinating ion, in particular the etherate of tetrafluoroboric acid, generally in the same solvent or in another solvent with the same characteristics. The catalytic solution thus obtained will then be used in the hydrogenation of substrate (II).

When a hydrogenation medium which comprises a solvent is used, preferably the same solvent as that in which the catalyst has been obtained is used. For this purpose, one can use a chlorinated hydrocarbon like dichloromethane, dichlororethane or a mixture of both. The use of dichloromethane, optionally in a mixture with the other solvents which have been cited above, has proved to be very advantageous according to the invention.

According to a particularly preferred embodiment of the process according to the present invention, methyl 3-oxo-2-pentyl-1-cyclopentene-1-acetate is used as a substrate in order to obtain Hedione® in the form of the preferred (+)-cis-configuration isomer.

The catalysts according to the present invention which have ligands of the DuPHOS type, and in particular Me-DuPHOS, have proved to be particularly useful for the hydrogenation of this substrate.

The hydrogenation which characterizes the process according to the invention is carried out under a hydrogen pressure which can vary from 10 to 100 bar (2 to $10 \times 10^6$ Pa). Pressures from 70 to 100 bar, in particular from 90 to 100 bar, are preferred.

The reaction may take place at temperatures of up to 50° to 60° C., or even 100° C. Preferably, one will work at room temperature or a lower temperature. It has been found that temperatures of down to −10° C., or even lower, made it possible to obtain very useful results.

The molar concentrations of the Ru(II) catalyst with respect to the substrate typically vary from 0.01 to 4 mole %, preferably from 0.1 to 2 mole %. According to a more preferred embodiment, they shall be of the order of 0.3 or 0.4 mole %.

Moreover, it has also been found that it is advisable to use solutions in which the substrate is concentrated, better results having been obtained when the concentration of the substrate in the hydrogenation medium was from about 0.4 to 1.5 molar, relative to the volume of said medium.

It is also possible to add a trialkylamine, preferably diisopropylethylamine (DIPEA), to this medium. It has in fact been observed that, under certain conditions, the hydrogenations carried out in the presence of the latter provided more useful results. The concentration in which this base may be added to the reaction medium varies in a molar ratio of from 0.1:1 to 0.5:1, relative to the Ru(II) catalyst. The best yields of final product were obtained when diisopropylamine was added in a proportion of 0.2 equivalents with respect to the catalyst.

According to a particular embodiment of the hydrogenation process according to the invention, in which the catalyst is formed in situ in the hydrogenation medium, the substrate which is to be hydrogenated is first mixed with the equimolar mixture of [(COD)Ru(2-methylallyl)$_2$] and diphoshine ligand, optionally in a solvent, and thereafter $HBF_4$-etherate or another salt of a HX acid is added to the thus obtained solution, in the proportion mentioned above. The thus obtained reaction medium is thereafter pressurized under hydrogen in a conventional manner, as will be described in the examples below. This etherate or another salt of the onium type can be added as such or in the form of a solution, and either in the same solvent as that previously used, or in a different solvent.

The invention thus provides new catalysts and processes for the use of these catalysts which allow the preparation, in a single step, and under conditions which are advantageous and susceptible of industrial application, of products useful in perfumery, in a stereoselective manner and, as the case may be, enantioselective, and in excellent yields. Unlike the prior art catalysts, the catalysts of the present invention are capable of hydrogenating substrates (II) with very fast reaction speeds, substrate conversion rates above 98% and providing essentially the diastereomer of (1R)-cis configuration of the desired compounds.

The invention will now be described in greater detail by means of the following examples, in which the temperatures are indicated in degrees centigrade (°C.) and the abbreviations have the meaning generally recognized in the art.

EMBODIMENTS OF THE INVENTION

EXAMPLE 1

Preparation of the catalysts
General Method

In a glove box under argon, at room temperature, a Schlenk tube was charged with equimolar amounts of [(COD)Ru(2-methylallyl)$_2$] or another complex of Ru, and the selected ligand. The dried and degassed solvent necessary to dilute this mixture was added. After 5 minutes, tetrafluoroboric acid etherate (or another onium salt), optionally in solution in the non-coordinating solvent, was added dropwise using a syringe, while the mixture was stirred using a Teflon® covered magnetic stirring rod. After stirring, a small amount of solvent was further added and stirring was maintained for about half an hour. The catalyst thus obtained in the form of a solution can be stored for several days in the glove box without losing its activity.

The solution may also be concentrated under vacuo to provide the catalyst in a solid form.

In a typical run, 0.20 mmole (64 mg) of [(COD)Ru(2-methylallyl)$_2$] (origin: Acros Organics) and 0.20 mmole (61 mg) of (−)-(R,R)-Me-DuPHOS or [(−)-1,2-bis-(2R,5R)-2,5-dimethylphospholano)-benzene; origin: Strem Chemicals] were reacted in 4 ml of $CH_2Cl_2$. A 0.10N solution (4 ml) of $HBF_4 \cdot Et_2O$ (Et=ethyl; 0.40 mmole) in $CH_2Cl_2$ was added. After stirring for 30 min, another 8 ml of $CH_2Cl_2$ were added, and stirring was continued for half an hour. The catalyst thus obtained was used as such in the hydrogenation reactions.

Optically active catalysts were thus prepared with the following ligands: (+)-(S,S)-Me-DuPHOS; (−)-(R,R)-Me-DuPHOS; (+)-(S,S)-Et-DuPHOS; (−)-(R,R)-Et-DuPHOS; (+)-(R)-BINAP; (−)-(S)-BINAP; (−)-(R,R)-NORPHOS; (−)-(S,S)-CHIRAPHOS; (+)-(R,R)-CHIRAPHOS; (−)-(S,S)-SKEWPHOS; (+)-(R,R)-SKEWPHOS; (−)-(R,R)-DIPAMP; (+)-(S,S)-DIPAMP; (−)-(S)-Tol BINAP; (+)-(R)-Tol BINAP; (−)-(R)-(S)-JOSIPHOS et (+)-(S)-(R)-JOSIPHOS. All of these ligands are commercially available or are prepared according to known methods.

Other catalysts which were prepared according to the method described above comprised ligands of the type L7 (R=methyl, ethyl or isopropyl), L8 [$R^1$=$(CH_3)_3Si$ and $R^2$=phenyl or isopropyl], L9 ($R^1$=$CH_3$ and $R^2$=phenyl), L10 (R=ethyl, isopropyl or phenyl), L11 (R=cyclohexyl and R'=phenyl), L12 (R=phenyl) and L13 (n=1, 2, 3 or 4).

The ligands L13 mentioned above are commercially available (origin: Fluka Chemie and Aldrich), as is the ligand of type L12 cited above (origin: Strem Chemicals). The above mentioned ligands of the L8, L9 and L10 type were prepared according to known methods (see references cited above and I. R. Butter et al., Synth. React. Inorg. Met. -Org. Chem. 1985, 15, 109) from ferrocene and according to the following reaction schemes:

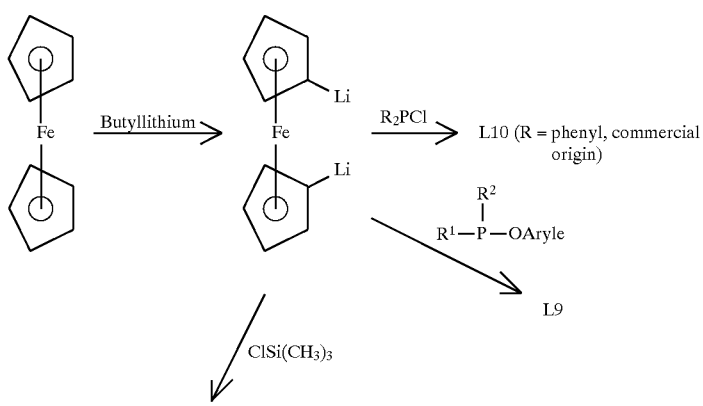

-continued

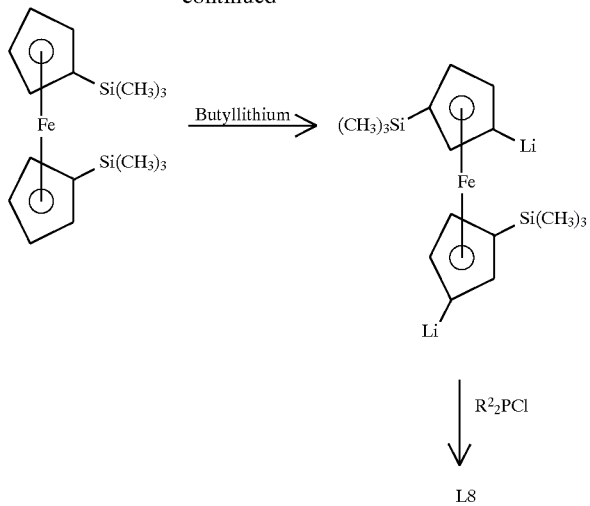

For the preparation of the ligands of type L7, one can use, for example, the method described in U.S. Pat. No. 5,171,892.

In the method of preparation of the catalyst described above, a solution of $HBF_4 \cdot Et_2O$ in diethyl ether (0.2M) was also used, giving similar results.

EXAMPLE 2

Hydrogenation of methyl 3-oxo-2-pentyl-1-cyclopentene-1-acetate

General method of hydrogenation

In a glove box under argon and at room temperature, a glass beaker adapted for use in an autoclave was charged with the catalyst solution obtained as described in example 1, the above-mentioned substrate which had been prior degassed, and the degassed solvent. The beaker containing a stirring rod was introduced in the autoclave inside the glove box, and the autoclave was sealed before being taken out of the glove box to be pressurized. The inlets of the autoclave were purged with $H_2$ and thereafter pressurized to the chosen value. The reaction was allowed to occur at room temperature. The pressure was released under air, the autoclave was opened and the solution concentrated under reduced pressure. The catalyst was precipitated with pentane, filtered and the filtrate was concentrated to provide the desired Hedione®. The product can be purified by distillation in a bulb-to-bulb apparatus (150°–200° C./5 Pa) without changing the diastereomeric ratio.

In a typical run, for example, there was used a $H_2$-pressure of 90 bar ($9 \times 10^6$ Pa), room temperature and a reaction time of 1.5 h for a substrate weight of 269 mg (1.20 mmole) and 1 ml of $CH_2Cl_2$, the catalyst being present at a ratio of 1 mole % relative to the substrate (1.0 ml of a solution of the (−)-(R,R)-Me-DuPHOS catalyst specifically described in example 1).

Table I below gives a summary of the results of the different runs which were carried out under various conditions and with catalysts which had been prepared as described in example 1, by means of the chiral ligands indicated in table I.

Replacing the ligands mentioned in this table by their respective enantiomers enabled the preparation of products in which the cis/trans ratio was identical to the value indicated in the table for the enantiomer in question, but wherein the ratio (+)-(cis)/(−)-cis and (−)-trans/(+)-trans was the reverse of that indicated in the table.

An analysis of this table shows that when using coordinating solvents such as methanol (runs 1 and 2) or yet mixtures of coordinating and non-coordinating solvents, either a bad yield in Hedione® or an unfavorable cis/trans ratio is obtained, in comparison with those runs which were carried out in, for example, dichloromethane. Moreover, when the substrate is too diluted (run 7), no hydrogenation is observed.

TABLE I

| Run | Ligand | Catalyst concentration (mole %) | Substrate concentration (M) | Reaction time (h) | Solvent and other conditions | $H_2$ pressure ($10^6$Pa) | Yield of Hedione® % | Isomer ratio cis/trans | Enantiomeric ratio (+)cis/(−)cis | Enantiomeric ratio (−)trans/(+)trans |
|---|---|---|---|---|---|---|---|---|---|---|
| 1 | (−)-Me-DuPHOS | 2 | 0.45 | 96 | MeOH/THF (3/1) | 9 | 55 | 9:91 | 80:20 | 80:20 |
| 2 | (−)-Et-DuPHOS | 2 | 0.45 | 96 | MeOH/THF (3/1) | 9 | 88 | 7:93 | 77:23 | 77:23 |
| 3 | (−)-Me-DuPHOS | 2 | 0.53 | 0.5 | $CH_2Cl_2$ | 9 | 99 | 97:3 | 80:20 | 61:39 |
| 4 | (−)-Me-DuPHOS | 1 | 0.53 | 1.5 | $CH_2Cl_2$ | 9 | 99 | 98:2 | 80:20 | 60:40 |
| 5 | (−)-Me-DuPHOS | 1 | 0.53 | 16.5 | T = −10° C. $CH_2Cl_2$ | 9 | 99 | 98:2 | 86:14 | 60:40 |
| 6 | (−)-Me-DuPHOS | 1 | 0.53 | 3.25 | $CH_2Cl_2$ | 4.5 | 80 | 98:2 | 80:20 | 53:47 |
| 7 | (−)-Me-DuPHOS | 1 | 0.04 | 68 | $CH_2Cl_2$ | 9 | 6.5 | 60:40 | 68:32 | 51:49 |
| 8 | (−)-Me-DuPHOS | 0.5 | 0.79 | 5 | $CH_2Cl_2$ | 9 | 99 | 98:2 | 80:20 | 58:42 |
| 9 | (−)-Me-DuPHOS | 0.25 | 1.18 | 16 | $CH_2Cl_2$ | 9 | 99 | 96:4 | 80:20 | 67:33 |
| 10 | (−)-Me-DuPHOS | 2 | 0.37 | 15 | toluene-$CH_2Cl_2$ | 9 | 4.5 | 45:55 | — | — |

TABLE I-continued

| Run | Ligand | Catalyst concentration (mole %) | Substrate concentration (M) | Reaction time (h) | Solvent and other conditions | $H_2$ pressure ($10^6$Pa) | Yield of Hedione ® % | Isomer ratio cis/trans | Enantiomeric ratio (+)cis/(−)cis | Enantiomeric ratio (−)trans/ (+)trans |
|---|---|---|---|---|---|---|---|---|---|---|
| 11 | (+)-(R,R)-SKEWPHOS | 2 | 0.53 | 3 | $CH_2Cl_2$ (1:2) | 10 | 24 | 95:5 | 75:25 | 58:42 |
| 12 | (−)-(S,S)-CHIRAPHOS | 2 | 0.53 | 2 | $CH_2Cl_2$ | 9 | 97 | 96:4 | 31:69 | — |
| 13 | (−)-(R,R)-NORPHOS | 2 | 0.53 | 2 | $CH_2Cl_2$ | 9 | 98 | 96:4 | 57:43 | — |
| 14 | (+)-(S,S)-DIPAMP | 2 | 0.53 | 2 | $CH_2Cl_2$ | 9 | 50 | 94:6 | 69:31 | — |
| 15 | L7 (R = $CH_3$) | 2 | 0.53 | 12 | $CH_2Cl_2$ | 5 | 98 | 97:3 | 67:33 | — |
| 16 | L7 (R = $C_2H_5$) | 2 | 0.53 | 12 | $CH_2Cl_2$ | 5 | 89 | 98:2 | 73:27 | — |
| 17 | L7 (R = isopropyl) | 2 | 0.53 | 12 | $CH_2Cl_2$ | 5 | 97 | 97:3 | 73:27 | — |
| 18 | LII (R = cyclohexyl R' = phenyl)) | 2 | 0.50 | 4.5 | $CH_2Cl_2$ | 9 | 98 | 98:2 | 77:23 | — |

EXAMPLE 3

The substrate mentioned in example 2 was hydrogenated according to a method analogous to that described above, by proceeding as follows.

In a glove box under argon and at room temperature, [(COD)Ru(2-methylallyl)$_2$] (16.5 mg; 0.051 mmole) was dissolved in dichloromethane (1 ml) and stirred for 2 min. To the resulting solution, a solution of (+)-R-BINAP [(+)-(R)-2,2'-bis (diphenylphosphino-1,1'-binaphtalene); 31.6 mg; 0.051 mmole; origin: Fluka Chemicals] in dichloromethane (2 ml) was added and stirred for about 30 min. Then tetrafluoroboric acid etherate (14 μl; origin: Fluka Chemie) was added. Having stirred for 30 min, a solution of methyl 3-oxo-2-pentyl-1-cyclopenteneacetate (0.5 g; 2.23 mmole) in dichloromethane (10 ml) was added and stirred for 30 min at room temperature. This solution, still under Ar, was charged in an autoclave which contained a glass beaker with a magnetic stirrer. After purging with $H_2$, the autoclave was pressurized at $9 \times 10^6$ Pa for 64 h at 20° C. After decompressing the orange solution was taken and concentrated under high vacuo. The residue was taken in pentane (2 ml) to precipitate the catalyst. The solution was filtered on a 0.45 μm acrodisc and concentrated. 500 mg of a transparent oil containing 93% Hedione®, with a cis/trans ratio of 72:28, and 6% of starting product were thus obtained. The enantiomeric ratios were as follows: (+)-cis/(−)-cis=73/27; (+)-(trans)/(−)-trans=35/65.

EXAMPLE 4

In a glove box under argon and at room temperature, 5.376 g (24 mmole) of the substrate cited in the above examples, 19.2 mg of [(COD)Ru(2-methylallyl)$_2$] (0.06 mmole), 0.06 mmole (18.4 mg) of (−)-Me-DuPHOS and 12 ml of $CH_2Cl_2$ were charged into a glass beaker adapted for use in an autoclave and equipped with a stirrer. Thereafter, 0.12 mmole of $HBF_4$ etherate (1.2 ml of a 0.1N solution in dichloromethane) were added. After stirring for 1 h, the beaker containing a stirring rod was introduced in the autoclave inside the glove box, and the autoclave was closed before being pressurized outside the glove box. The inlets of the autoclave were purged with $H_2$ and thereafter pressurized at $2 \times 10^6$ Pa. The reaction was allowed to proceed at room temperature for 17 h. The autoclave was degassed and opened and the solution concentrated under reduced pressure. The catalyst was precipitated with pentane, filtered and the resulting filtrate concentrated to obtain the desired Hedione®. The product thus obtained (yield 99%) showed the following isomer ratios: cis/trans=97/3 ; (+)-cis/(−)-cis= 80/20.

EXAMPLE 5

The reaction was carried out in a similar manner to that described in examples 2 to 4, but 2.2 equivalents of tetrafluoroboric acid (from a 0.2M solution. of $HBF_4$ etherate in diethyl ether) per mole of Ru(II) complex were used in the preparation of the catalyst which was carried out analogously to the way described in example 1.

Moreover, in the runs which are summarized in the tables below, the catalyst was used in solid form. Thus, methyl 3-oxo-2-pentyl-1-cyclopentene-1-acetate (0.5 mmole in 2 ml of $CH_2Cl_2$) was hydrogenated in the presence of the amount of solid catalyst indicated in the tables.

Table II below summarizes the results which were obtained in the hydrogenation reactions carried out with different catalysts (variation of the nature of the ligand) in the concentrations indicated, a hydrogen pressure of about 100 bar ($10 \times 10^6$ Pa), room temperature and a reaction time of about 22 h.

Table III summarizes the results which were obtained with different catalysts (variation of the nature of the ligand) and by varying several reaction parameters. All reactions were carried out at room temperature, unless otherwise indicated.

TABLE II

| Run | Ligand | Catalyst concentration (mole %) | Solvent | Yield of Hedione ® % | Isomer ratio cis/trans | Enantiomeric ratio (+)cis/(−)cis | Enantiomeric ratio (−)trans/(+)trans |
|---|---|---|---|---|---|---|---|
| 1 | (−)-Me-DuPHOS | 2 | MeOH | 31 | 32:68 | 80:20 | 78:22 |
| 2 | (−)-Me-DUPHOS | 2 | MeOH + triethylamine* | 9.1 | 72:28 | 65:35 | 54:46 |
| 3 | (−)-Me-DUPHOS | 2 | triethylamine** + | 4.5 | 68:32 | 55:45 | 41:59 |

TABLE II-continued

| Run | Ligand | Catalyst concentration (mole %) | Solvent | Yield of Hedione ® % | Isomer ratio cis/trans | Enantiomeric ratio (+)cis/(−)cis | Enantiomeric ratio (−)trans/(+)trans |
|---|---|---|---|---|---|---|---|
| 4 | (−)-Me-DuPHOS | 2 | MeOH THF | 5.5 | 61:39 | 63:37 | 56:44 |
| 5 | (−)-Me-DuPHOS | 2 | $CH_2Cl_2$ | 100 | 82:18 | 80:20 | 77:23 |
| 6 | (−)-Et-DuPHOS | 1 | $CH_2Cl_2$ | 77 | 80:20 | 70:30 | 73:27 |
| 7 | (+)-BINAP | 1 | $CH_2Cl_2$ | 77 | 74:26 | 71:29 | 65:35 |
| 8 | (−)-Me-DUPHOS | 1 | $CH_2Cl_2$ | 91 | 79:21 | 79:21 | 77:23 |

*1 equivalent per mole of catalyst
**2 equivalents per mole of catalyst

TABLE III

| Run | Ligand | Catalyst concentration (mole %) | Reaction time (h) | Solvent | $H_2$ pressure ($10^6$Pa) | Yield of Hedione ® % | Isomeric ratio cis/trans | Enantiomeric ratio (+)cis/(−)cis | Enantiomeric ratio (−)trans/(+)trans |
|---|---|---|---|---|---|---|---|---|---|
| 1 | (−)-Me-DuPHOS | 1.0 | 14.5 | $CH_2Cl_2$ | 10 | 93 | 94:6 | 80:20 | 72:28 |
| 2* | (−)-Me-DUPHOS | 4.0 | 6.0 | $CH_2Cl_2$ | 9 | 90 | 86:14 | 83:17 | 79:21 |
| 3 | (−)-Me-DuPHOS | 1.0 | 40.0 | $CH_2Cl_2$ | 10 | 95 | 75:25 | 79:21 | 77:23 |
| 4 | (−)-Me-DuPHOS | 1.0 | 40 | $CH_2Cl_2$ + DIPEA$^{a)}$ (0.2 eq.) | 10 | 95 | 82:18 | 79:21 | 76:24 |
| 5 | (−)-Me-DuPHOS | 2.0 | 2 | $CH_2Cl_2$ + DIPEA$^{a)}$ (1.0 eq.) | 9 | 43 | 96:4 | 80:20 | 56:44 |
| 6 | (−)-Me-DuPHOS | 2.0 | 2 | $CH_2Cl_2$ + DIPEA$^{a)}$ (2.0 eq.) | 9 | 2,1 | 59:41 | 46:54 | 60:40 |
| 7** | (−)-Me-DuPHOS | 2.0 | 2 | $CH_2Cl_2$ + DIPEA$^{a)}$ (0.2 eq.) | 9 | 98 | 97:3 | 81:19 | 64:36 |
| 8 | (−)-(R,R)-DIPAMP | 2.0 | 2 | $CH_2Cl_2$ + DIPEA$^{a)}$ (0.2 eq.) | 9 | 50 | 94:6 | 31:69 | 52:48 |
| 9 | (−)-(S)-TolBINAP | 2.0 | 2 | $CH_2Cl_2$ + DIPEA$^{a)}$ (0.2 eq.) | 8 | 88 | 96:4 | 31:69 | 48:52 |

$^{a)}$diisopropylethylamine
*Temperature 0–5° C.
**Substrate degassed before hydrogenation

EXAMPLE 6

In a glove box under argon and at room temperature, 38 mg of [(COD)Ru(2-methylallyl)$_2$] (0.12 mmole) and 36 mg (0.12 mmole) of (−)-Me-DuPHOS were dissolved in 5.38 g (24 mmole) of methyl-3-oxo-2-pentyl-1-cyclopentene-acetate in a glass beaker adapted for use in an autoclave which was equipped with a stirrer. Thereafter, 39 mg of HBF$_4$ etherate (0.24 mmole; 32.7 µl, syringe) were gently added under stirring. After stirring for 4 h, 3.4 ml of this catalytic solution (containing about 0.075 mmole of catalyst) were transferred to another beaker, and another 8.38 g (37.4 mmole) of methyl 3-oxo-2-pentyl-1-cyclopentene-1-acetate (total amount about 53 mmole) were added to this. Working as previously described, the substrate was hydrogenated at a H$_2$ pressure of 5×10$^6$ Pa. The reaction was allowed to proceed for 20 h at room temperature. The autoclave was degassed, opened, and the catalyst was precipitated using pentane, filtered and the filtrate concentrated to obtain the desired Hedione®. The thus obtained product (yield 99% based on the above mentioned substrate) showed the following isomer ratios: cis/trans=97/3: (+)-cis/(−)-cis= 80/20, 60% e.e.

By working under similar conditions but varying the nature of the solvent used in the hydrogenation, i.e. of the solvent of the mixture of [(COD)Ru(2-methallyl)$_2$] and (−)-Me-DuPHOS, as well as that of the solvent of the tetrafluoroboric acid etherate, the results given in the table below were obtained. The hydrogenated substrate (II) was always methyl 3-oxo-2-pentyl-1-cyclopentene-1-acetate, and the catalyst concentration was about 2 mole % relative to the mentioned substrate, unless otherwise indicated.

When the tetrafluoroboric acid etherate is used in solution, its concentration in the solution is always about 0.1M (moles/l).

Yields of the order of 99% in Hedione®, based on starting substrate (II) present in the hydrogenation medium, were systematically obtained. Of course, when ratios of catalyst/substrate of the order of 0.5 mole % or less were used, prolonged reaction times (in the range from 6 to 20 h) were necessary to obtain a complete and quantitative conversion of the substrate, while hydrogenation times of 1 to 3 h in general were sufficient to obtain this result when the catalyst was present in concentrations of the order of 1 mole % or more, with respect to the substrate.

Every time, almost no losses were observed, only traces of residues (~1%) being obtained when the hydrogenation product was distilled in a bulb to bulb apparatus or a Leybold distillation apparatus ("thin-film distillation").

TABLE IV

| Run | Hydrogenation solvent | Solvent for $HBF_4.Et_2O$ | Isomer ratio cis/trans | Enantiomer ratio (+)-cis/(−)-cis |
|---|---|---|---|---|
| 1 | dichloroethane | dichloroethane | 99:1 | 70:30 |
| 2 | methyl pivalate | dichloromethane | 98.9:1.1 | 76:24 |
| 3 | ethyl acetate | dichloromethane | 99.3:0.7 | 73:27 |
| 4 | isopropyl acetate | dichloromethane | 99.3:0.7 | 72:28 |
| 5 | 2-butanone | dichloromethane | 98.9:1.1 | 79:21 |
| 6 | methyl acetate | methyl acetate | 98.5:1.5 | 75:25 |
| 7 | methyl acetate | methyl acetate/dichloromethane | 99.3:0.7 | 74:26 |
| 8 | methyl acetate | dichloromethane | 99:1 | 77:23 |
| 9 | methyl acetate/DHH* | methyl acetate | 98.5:1.5 | 75:25 |
| 10 | acetone | dichloromethane | 99.5:0.5 | 79:21 |
| 11 | DHH* | methyl acetate | 98.2:1.8 | 81:19 |
| 12 | DHH* | — | 98.2:1.8 | 81:19 |
| 13 | 3-pentanone | dichloromethane | 98.9:1.1 | 79:21 |
| 14 | tetrahydrofurane | dichloromethane | no hydrogenation observed | |
| 15 | toluene | dichloromethane | no hydrogenation observed | |
| 16 | N-methylformamide | dichloromethane | no hydrogenation observed | |
| 17 | N,N-dimethylformamide | dichloromethane | no hydrogenation observed | |
| 18 | sulfuric ether | dichloromethane | very slow reaction | |
| 19 | chloroform | chloroform | no hydrogenation observed | |
| 20 | methyl-2-methyl-proponoate | dichloromethane | very slow reaction | |
| 21** | DHH* | — | 96.7:3.3 | 80:20 |

*methyl 3-oxo-2-pentyl-1-cyclopentene-1-acetate
**catalyst concentration 0.15 mole %

EXAMPLE 7

The reaction was carried out analogously to that described in example 6, but using 100 g (446 mmole) of methyl 3-oxo-2-pentyl-1-cyclopentene-acetate, 427 mg (1.34 mmole) of [(COD)Ru(2-methylallyl)$_2$], 410 mg (1.34 mmole) of (−)-Me-DuPHOS and 26.5 ml of $HBF_4.O(C_2H_5)_2$ in dichloromethane (0.1M, 2.68 mmole). This corresponds to a catalyst concentration of 0.3 mole %, relative to the substrate. 170 ml of dichloromethane were added, and the mixture was hydrogenated at a temperature of 7.5° C. and a pressure of $5×10^6$ Pa for 70 h to obtain methyl (+)-(1R)-cis-3-oxo-2-pentyl-1-cyclopentaneacetate in 99% yield, cis/trans ratio=99.2/0.8 and (+)-cis/(−)-cis ratio=84/16.

EXAMPLE 8

The catalysts according to the invention were prepared using (−)-Me-DuPHOS as ligand and varying on the nature of the acid of formula HX.

Thereafter, 6.4 mg of [(COD)Ru(2-methylallyl)$_2$] (0.02 mmole), 6.4 mg of (−)-Me-DuPHOS (0.021 mmole) and 0.224 g of methyl 3-oxo-2-pentyl-1-cyclopenteneacetate in 2 ml of dichloromethane were charged into a reactor. The solution thus obtained was treated with 0.20 or 0.16 ml (2 or 1.6 molar equivalents of ruthenium complex) of the above-mentioned acid solution.

The mixture was thereafter hydrogenated at room temperature and $10×10^6$ Pa to give the results summarized in the table below. It should be noticed that the runs were not optimized, which explains the poor results obtained in some cases.

| Run | Acid | Acid equivalents | Reaction time (h) | Yield of Hedione ® | Cis/trans ratio | (+)-Cis/(−)-cis ratio | (−)-Trans/(+)-trans ratio |
|---|---|---|---|---|---|---|---|
| 1 | $HBF_4$ | 2 | 3 | 99.4 | 88:12 | 81:19 | 79:21 |
| 2 | $HBF_4$ | 1.6 | 3 | 98.7 | 87:13 | 82:18 | 81:19 |
| 3 | $HAsF_6$ | 2 | 3.5 | 78.7 | 56:44 | 79:21 | 78:22 |
| 4 | $HAsF_6$ | 1.6 | 3.5 | 99.3 | 82:18 | 78:22 | 78:22 |
| 5 | $HPF_6$ | 2 | 2 | 2.9 | 51:49 | 57:43 | 60:40 |
| 6 | $HPF_6$ | 1.6 | 2 | 80.8 | 86:14 | 71:29 | 69:31 |
| 7 | $HSbF_6$ | 2 | 3 | 98.3 | 48:52 | 75:25 | 74:26 |
| 8 | $HSbF_6$ | 1.6 | 3 | 99.0 | 84:16 | 75:25 | 74:26 |

The respective acids $HBF_4$, $HPF_6$, $HSbF_6$ and $HAsF_6$ (as etherates) were prepared by reacting 0.2 mmole of the corresponding silver salt in 0.8 ml of dichloromethane, using 0.2 ml of a 1M anhydrous solution of HCl 1M in ether.

The silver chloride formed precipitated immediately, and 1 ml of a 0.2M solution of the respective acid, i.e. $HBF_4$, $HPF_6$, $HSbF_6$ or $HAsF_6$, was obtained.

Similar results were obtained when diisopropylethylamine [0.040 ml of a 0.1M solution; 20 mole % with respect to Ru(II)] was added to the hydrogenation medium. Improvement (of the order of 10%) of the cis/trans isomer ratio was then observed.

EXAMPLE 9

The activity of a variety of racemic or achiral catalysts according to the invention, prepared as described in example 1, using $HBF_4$ as the acid (in the form of its etherate), and varying the ligand, was tested in the hydrogenation reaction of methyl 3-oxo-2-pentyl-1-cyclopentene-acetate.

All hydrogenations were carried out in dichloromethane and at room temperature. The results are given in the table. It should be noticed that these runs were not optimized, which explains the poor substrate conversions observed in some cases.

filter of 0.22 $\mu$ to precipitate the catalyst. The remaining solid was washed with pentane and filtered through the same filter. The combined pentane solutions contained the desired Hedione® in a cis/trans ratio=98.5/1.5 and a ratio (+)-cis/(−)-cis=79/21.

D. A second hydrogenation cycle was carried out with the catalyst which had remained in the Teflon® filter. The latter was washed with 2 ml of $CH_2Cl_2$ and the same dichloromethane used to dissolve the precipitate which

| Run | | Ligand | Catalyst concentration (mole %) | Reaction time (h) | $H_2$ pressure ($10^6$Pa) | Conversion of substrate (%) | Isomer ratio cis/trans |
|---|---|---|---|---|---|---|---|
| 1 | | L13 (n = 1) | 2 | 4 | 5 | 9 | 94:6 |
| 2 | | L13 (n = 2) | 2 | 6 | 5 | 18 | 96.6:3.4 |
| 3 | | L13 (n = 3) | 2 | 6 | 5 | 18 | 96.6:3.4 |
| 4 | | L13 (n = 4) | 2 | 4 | 5 | 35 | 98.8:1.2 |
| 5 | | L10 (R = $C_6H_5$) | 2 | 14.5 | 5 | 29 | 98:2 |
| 6 | | L10 (R = isopropyl) | 1 | 3 | 5 | 53 | 98.9:1.1 |
| 7* | | L10 (R = isopropyl) | 2 | 7.5 | 5 | 98.5 | 96.8:3.2 |
| 8 | | L10 (R = $C_2H_5$) | 1 | 17 | 5 | 4 | 81:19 |
| 9** | | L12 (R = $C_6H_5$) | 2 | 25 | 9 | 96 | 91.3:8.2 |
| 10 | L8 | ($R^1$ = Si(CH$_3$)$_3$, $R^2$ = $C_6H_5$) | 2 | 5 | 5 | 30 | 98.3:1.7 |
| 11 | L8 | ($R^1$ = Si(CH$_3$)$_3$, $R^2$ = isopropyl) | 2 | 22 | 9 | 92 | 97.0:3.0 |
| 12 | L8 | ($R^1$ = Si(CH$_3$)$_3$, $R^2$ = isopropyl) | 1 | 8 | 4 | 43 | 98.3:1.7 |
| 13 | L8 | ($R^1$ = $CH_3$, $R^2$ = $C_6H_5$) | 2 | 24 | 9 | 15 | 94.4:5.6 |

*25% of alcohols resulting from the reduction of Hedione ® (by-products)
**7% of alcohols resulting from the reduction of Hedione ® (by-products)

EXAMPLE 10

A. In a glove box under argon, 4.05 g of $HBF_4.Et_2O$ (Et=$C_2H_5$; 25.0 mmole, 3.40 ml) were introduced into a glass beaker using a pipette, then about 100 ml of dichloromethane were added. Thereafter the mixture was stirred to dissolve the etherate and the beaker was filled up to a volume of 250 ml. The 0.1M (moles/l) solution of $HBF_4.Et_2O$ thus obtained was used as such for the preparation of the catalyst.

B. In a glove box, 16.0 mg (0.050 mmole) of [Ru(COD)(2-methallyl)$_2$] and 15.0 mg (0.050 mmole) of (−)-Me-DuPHOS were mixed in a glass container and dissolved in 4 ml of $CH_2Cl_2$. Thereafter, 1 ml (0.1 mmole) of the $HBF_4$ etherate solution prepared in step A was added slowly (about 1 min) at room temperature via a syringe. The resulting red-brown solution containing about 0.01M (moles/l) of catalyst was allowed to stand for 2 h before use. The solution stays active for more than 1 week when kept in the glove box at room temperature.

C. Inside the glove box, 224 mg (1 mmole) of methyl 3-oxo-2-pentyl-1-cyclopentene-1-acetate were added to 2 ml of the catalytic solution obtained in step B (0.02 mmole, 2 mole % with respect to the substrate) in a glass beaker which can be transferred to an autoclave. The solution thus obtained was then transferred into an autoclave and stirred for 2 h at 90 bar (9×$10^6$ Pa) hydrogen pressure at room temperature. The autoclave was almost entirely degassed and opened inside the glove box. The yellow-orange reaction mixture was evaporated under vacuo to strip the dichloromethane. The solid residue and the yellow-orange liquid thus obtained were treated with pentane and the suspension filtered through a Teflon® had remained in the container. 224 mg of the substrate mentioned in C were added to this solution, which was thereafter hydrogenated as described in C to again obtain Hedione® with a cis/trans ratio of 98.8/1.2 and a (+)-cis/(−)-cis ratio of 79/21.

B'. According to an alternative embodiment to the one described under B, the catalyst was also prepared as follows: the $HBF_4.Et_2O$ solution in dichloromethane described under A was first added to (−)-Me-DuPHOS, and the ether and the dichloromethane were evaporated. The thus obtained solid of the onium salt of the ligand was then redissolved in pure dichloromethane and added to [Ru(COD)( 2-methallyl)$_2$]. The reaction occurs with release of isobutene. The catalyst thus obtained was used under conditions identical to those described under C to give (+)-cis-Hedione® having the same characteristics.

C' Results similar to those described under C were obtained when bis(2,4-dimethylpentadienyl)ruthenium (see, for example, L. Stahl et al., Organometallics, 1983, 2, 1229) or bis(2,4-dimethyl-1-oxapentadienyl)ruthenium (see T. Schmidt et al., J. Chem. Soc. Chem. Comm., 1991, 1427) were used for the preparation of the catalyst, instead of the complex [Ru(COD)(2-methallyl)$_2$].

C". Moreover, the use in the hydrogenation described under C of a catalyst prepared in a manner identical to that described under B but using as ligand (−)-JOSIPHOS (ligand L11, R=cyclohexyl, R'=phenyl; origin: STREM Chemicals Inc.) enabled the preparation of Hedione® with a cis/trans ratio of 98/2 and a (+)-cis/(−)-cis ratio of 77/23.

EXAMPLE 11

The reaction was carried out in a way similar to that described in Examples 10A to C, but using 4.171 g (13.056 mmole) of [Ru(COD)(2-methallyl)$_2$], 4.000 g (13.056 mmole) of (−)-Me-DuPHOS, 1000 g (4.458 mole) of methyl 3-oxo-2-pentyl-1-cyclopentene-1-acetate, 261 ml (26.10 mmole) of the 0,1M HBF$_4$.Et$_2$O-solution in dichloromethane and 1.71 of CH$_2$Cl$_2$.

The hydrogenation reaction was carried out at 7,5° C. and under a hydrogen pressure of 35 bar (3.5×10$^6$ Pa) for 24 h, under stirring (1000–2000 rpm).

After evaporation of the solvent, 1095 g of a brown product were obtained which were treated with pentane and the solution filtered as previously described. The combined pentane extracts were concentrated under vacuo to give 978 g of product, the thin-film distillation of which (Leybold type apparatus, 86°/0.1 mbar) gave 932 g of a colourless product consisting of the desired Hedione® having a cis/trans ratio of 98/2 and a (+)-cis/(−)-cis ratio of 85/15.

We claim:

1. Ruthenium (II) catalyst comprising ligands formed of bidentate phosphines, characterized in that it is obtainable by a process which comprises treating an appropriate Ru(II) complex and a bidentate diphosphine ligand, present in equimolar amounts, with an acid of formula HX, wherein X is a non-coordinating anion, said acid being used in a ratio which does not exceed 2 molar equivalents per mole of the Ru(II) complex, the treatment being carried out in a non-coordinating or weakly coordinating medium and under an inert atmosphere.

2. Catalyst according to claim 1, characterized in that the Ru(II) complex is selected from the group of Ru(II) compounds of the type (diene)Ru(allyl)$_2$ or bis(pentadienyl)Ru.

3. Catalyst according to claim 2, characterized in that the ruthenium complex is (COD)Ru(2-methallyl)$_2$, bis(2,4-dimethylpentadienyl)Ru or bis(2,4-dimethyl-1-oxapentadienyl)Ru.

4. Catalyst according to claim 1, characterized in that the diphosphine ligand is selected from the group consisting of the chiral ligands known under the abbreviations of Me-DuPHOS, Et-DuPHOS, BINAP, To1BINAP, SKEWPHOS and JOSIPHOS.

5. Catalyst according to claim 4, characterized in that the bidentate phosphine ligand is selected from the group consisting of the chiral diphosphines known under the abbreviations of Me-DuPHOS, SKEWPHOS and JOSIPHOS.

6. Catalyst according to claim 5, characterized in that the ligand is (R,R)-(−)-Me-DuPHOS.

7. Catalyst according to claim 1, characterized in that the acid is selected from the group consisting of HBF$_4$, HPF$_6$, HSbF$_6$, HAsF$_6$, and HB{3,5-(CF$_3$)$_2$C$_6$H$_4$}$_4$.

8. Catalyst according to claim 7, characterized in that HBF$_4$ is used in the form of its etherate.

9. Catalyst according to claim 7, characterized in that the acid is used in a proportion of 1.5 to 2 molar equivalents per mole of Ru(II) complex.

10. Catalyst according to claim 1, characterized in that the treatment is carried out in presence of a non-coordinating or weakly coordinating organic solvent and/or of a substrate of formula

wherein R$^1$ represents a linear or branched alkyl radical from C$_1$ to C$_4$ and R$^2$ represents a saturated or unsaturated, linear or branched hydrocarbon rest from C$_1$ to C$_8$.

11. Catalyst characterized in that the treatment is carried out only in the presence of a substrate of formula (II) as defined in claim 10.

12. Catalyst according to claim 10, characterized in that the solvent is selected from the group consisting of dichloromethane, dichloroethane, methyl pivalate, methyl acetate, ethyl acetate, isopropyl acetate, acetone, 2-butanone, 3-pentanone and any mixture of said solvents.

13. Catalyst according to claim 12, characterized in that the solvent is or comprises dichloromethane.

14. Catalyst according to claim 10, characterized in that the substrate of formula (II) is methyl 3-oxo-2-pentyl-1-cyclopentene-1-acetate.

15. Catalyst according to claim 1, characterized in that the treatment is carried out at room temperature.

16. Process for the preparation of a catalyst of Ru(II), characterized in that equimolar amounts of an appropriate Ru(II) complex and of a bidentate phosphine ligand are reacted, under an inert atmosphere and in a non-coordinating or weakly coordinating medium, with an acid of formula HX, wherein X represents a non-coordinating anion, said acid being used in a proportion not exceeding 2 molar equivalents per mole of Ru(II) complex.

17. Process according to claim 16, characterized in that the reaction is carried out in the presence of an organic non-coordinating or weakly coordinating solvent and/or a substrate of formula

wherein R$^1$ is a linear or branched alkyl radical from C$_1$ to C$_4$ and R$^2$ is a saturated or unsaturated, linear or branched hydrocarbon rest from C$_1$ to C$_8$.

18. Process for the preparation of a compound of formula

wherein R$^1$ represents a linear or branched alkyl radical from C$_1$ to C$_4$ and R$^2$ represents a saturated or unsaturated, linear or branched hydrocarbon rest from C$_1$ to C$_8$, essentially in the form of the cis-configuration isomer, characterized in that a substrate of formula

in which R$^1$ and R$^2$ have the meaning indicated above, is hydrogenated in the presence of a Ru(II) catalyst according to claims 1, at a hydrogen pressure from 10 to 100 bar.

19. Process according to claim 18, characterized in that there is used a catalyst comprising as a ligand an appropriate chiral diphosphine, to obtain compound (I) essentially in the form of an optically active isomer of (1R)-cis configuration.

20. Process according to claim 18, characterized in that the catalytic hydrogenation is carried out in a non-coordinating or weakly coordinating solvent under the reaction conditions.

21. Process according to any of claims 18, characterized in that the Ru(II) catalyst is formed in situ, optionally in the presence of the substrate of formula (II).

22. Process according to claim 20, characterized in that the non-coordinating solvent is selected from the group consisting of dichloromethane, dichloroethane, methyl pivalate, methyl acetate, ethyl acetate, isopropyl acetate, acetone, 2-butanone, 3-pentanone, and any mixture of said solvents.

23. Process according to any of claims 18, characterized in that the substrate of formula (II) is methyl 3-oxo-2-pentyl-1-cyclopentene-1-acetate and in that essentially methyl (+)-(1R)-cis-3-oxo-2-pentyl-1-cyclopentaneacetate is obtained.

24. Process according to claim 23, characterized in that the hydrogenation is carried out in the presence of a catalyst selected from the group consisting of the chiral diphosphines known under the abbreviations of Me-DuPHOS, Et-DuPHOS, BINAP, Tol BINAP, SKEWPHOS, and JOSIPHOS.

25. Process according to any of claim 18, characterized in that the catalyst is present in a concentration from 0.1 to 2 mole %, with respect to the substrate.

26. A catalyst prepared by the process of claim 16.

* * * * *

UNITED STATES PATENT AND TRADEMARK OFFICE
CERTIFICATE OF CORRECTION

PATENT NO. : 5,874,600
DATED : February 23, 1999
INVENTOR(S) : Valentin Rautenstrauch, et al.

It is certified that error appears in the above-identified patent and that said Letters Patent is hereby corrected as shown below:

Column 5, line 42, change "or R = R' =cyclohexyl, phenyl" to --or R ≠ R' = cyclohexyl, phenyl--.

Column 11, line 44, change "2" to --$10^6$--.

Signed and Sealed this

Eighteenth Day of May, 1999

Attest:

Attesting Officer

Q. TODD DICKINSON

Acting Commissioner of Patents and Trademarks

UNITED STATES PATENT AND TRADEMARK OFFICE
CERTIFICATE OF CORRECTION

PATENT NO. : 5,874,600

DATED : February 23, 1999

INVENTORS : Valentin Rautenstrauch et al.

It is certified that error appears in the above-identified patent and that said Letters Patent is hereby corrected as shown below:

Column 6, lines 1-12, replace formula "(L8)" with the following:

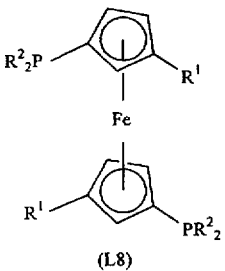

(L8)

Column 6, lines 20-30, replace formula "(L9)" with the following:

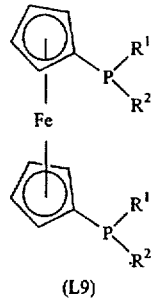

(L9)

UNITED STATES PATENT AND TRADEMARK OFFICE
CERTIFICATE OF CORRECTION

PATENT NO. : 5,874,600
DATED : February 23, 1999
INVENTOR(S) : Valentin Rautenstrauch, et al It is certified that error appears in the above-identified patent and that said Letters Patent is hereby corrected as shown below:

Column 11, line 53: change "To 1BINAP" to --TolBINAP--.

Column 14, line 21: change "To 1BINAP" to --TolBINAP--.

Column 17, Table 1, for "Run 18": change "LII" to -- L11--.

Signed and Sealed this

Fourteenth Day of September, 1999

Q. TODD DICKINSON

*Attest:*

*Attesting Officer*     Acting Commissioner of Patents and Trademarks